United States Patent
Martin et al.

[11] Patent Number: 6,119,032
[45] Date of Patent: *Sep. 12, 2000

[54] METHOD AND SYSTEM FOR POSITIONING AN INVASIVE DEVICE BY MAGNETIC RESONANCE (MR) IMAGING OF AN MR VISIBLE DEVICE

[75] Inventors: Alastair J. Martin, St. Louis Park, Minn.; Johannes J. Van Vaals, Eindhoven, Netherlands

[73] Assignee: U.S. Philips Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/002,561

[22] Filed: Dec. 31, 1997

[51] Int. Cl.$^7$ .......................................................... A61B 5/05

[52] U.S. Cl. .......................... 600/411; 600/414; 600/417; 606/130

[58] Field of Search ............................ 606/130; 600/411, 600/414, 417, 426, 427, 429

[56] References Cited

U.S. PATENT DOCUMENTS

| | | | |
|---|---|---|---|
| 5,517,990 | 5/1996 | Kalfas et al. | 600/414 |
| 5,647,361 | 7/1997 | Damadian | 128/683.2 |
| 5,682,890 | 11/1997 | Kormos et al. | 600/417 |

*Primary Examiner*—Ruth S. Smith
*Attorney, Agent, or Firm*—Dwight Renfrew

[57] ABSTRACT

The invention relates to MR guided intervention. For biopsies and similar interventions the challenge is to align a needle or other interventional device along an anticipated trajectory which hits a target point but does not intersect sensitive structures between the target and the surface. The invention includes the following method in order to position an MR visible device: collection of pre-intervention MR-images, establishing of an anticipated trajectory and an entry point by imaging of the MR-visible device and a thick slab positioned parallel to the surface and displaying of the MR localizer in the MR-image of the slab and moving the MR visible localizer to the entry point, imaging of two mutual orthogonal slices passing through the anticipated trajectory between the entry point and the target point and establishing an angle of entry by using for example a MR-visible pen and a targeting device.

10 Claims, 4 Drawing Sheets

METHOD AND SYSTEM FOR POSITIONING AN INVASIVE DEVICE BY MAGNETIC RESONANCE (MR) IMAGING OF AN MR VISIBLE DEVICE

BACKGROUND OF THE INVENTION

1. Field of the Invention

The invention relates to a method for positioning a magnetic resonance (MR) visible device in a body by means of magnetic resonance imaging, the method comprises the steps of providing a collection of MR images of the interior of a part of the body and selection of a target in the body and an entry point in the part of the body from the collection MR images. The invention further relates to an MR system comprising an MR apparatus and an MR-visible device, the MR-apparatus comprising, means for generating a static magnetic field, means for generating RF pulses and means for generating magnetic field gradient pulses, means for receiving MR-signals and means for processing the signals measured to an image, a control unit for generating control signals for the means for generating RF-pulses, the means for generating magnetic field gradient pulses, the means for receiving MR signals. In this application MR visible device means a device comprising means to be imaged in magnetic resonance images obtained from the device.

2. Description of Related Art

Such a method is known from U.S. Pat. No. 5,647,361. The known method is used for MR guided intervention. For biopsies and similar interventions an MR visible device, for example an MR visible invasive device is guided along the anticipated trajectory to a target without intersecting sensitive structures between the surface of the body and the target, such as major blood vessels or brain tissue with essential functionality. In the known method the anticipated trajectory from the entry point to the target in a body is selected from a collection of pre-intervention images. Thereto at least one pre-intervention image is obtained from the region comprising the target in the body. From the at least one or more pre-intervention images the target is determined and an entry point is determined. In a next step of the known method the MR visible device is introduced in the body at the selected entry point and guided to the target by MR imaging of the MR-visible device. A drawback of the known method is that the pre-intervention images may not actually represent a tissue location at the time of an actual intervention and the sensitive structures between the target and surface may be intersected.

SUMMARY OF THE INVENTION

It is inter alia an object of the invention to reduce the risk that sensitive structures are intersected in particular to provide technical means to support an operator to reduce said risk. To this end a method in accordance with the invention is characterised in that for establishing of the anticipated trajectory between the target and the entry point in the body the method comprises further steps of obtaining entry MR-images of an MR-visible device and a first portion of the body comprising, at least, a part of the anticipated trajectory near the entry point. In this way information on the actual position of the MR visible device and the surrounding tissue in the first portion of the body can be updated by real time MR imaging and the anticipated trajectory can be established by a medical decision from the entry-images in such a way that the anticipated trajectory is chosen without intersection of sensitive structures between the surface and the target, even as physiological changes of the tissue appear in the first portion between the instant of the pre-intervention imaging and the instant of the actual intervention.

A particular version of the method in accordance with the invention is characterised in that the first portion of the body comprises a slab parallel to a surface of the body through the entry point. In this way the entry point can be localised at the body at the instant just before the intervention taking into account information of a possible change of the tissue location during the actual intervention and the instant of obtaining pre intervention images, so the MR-visible device can be positioned at the entry point.

Another version of the method according with the invention is characterised in that the method comprises further steps of obtaining first entry angle MR images from a second portion of the body comprising the anticipated trajectory and a first area near the entry point, drawing of a line in the first entry angle MR images representing the anticipated trajectory in the first entry angle MR images and manipulating an MR visible invasive device at the actual entry point such that the MR visible invasive device becomes aligned with the line. These steps comprise technical means for supporting the operator in the establishment of an entry angle of the MR-visible device at the entry point. The second portion of the body may coincide with the first portion of the body.

Another version of the method in accordance with the invention is characterised in that for establishing an angle of entry at the actual entry point the method comprises further steps of obtaining second entry angle images from a third portion comprising the anticipated trajectory and a second area near the entry point, the third portion intersecting the second portion through the anticipated trajectory and manipulating the MR visible device such that it is imaged simultaneously in both the first and second entry angle images. In this way the MR visible device is visible in both the first and second entry angle images when it is aligned with the anticipated trajectory. These steps comprise also technical means for support of the operator in the establishment of an angle of entry at the actual entry point. For example, said second and third portions comprises two orthogonal slabs both comprising the anticipated trajectory.

A further version of the method in accordance with the invention is characterised in that for guiding an MR visible invasive device along the anticipated trajectory the method comprises a step of introducing the MR visible invasive device in the body while the MR visible invasive device remains aligned to the line in the first entry angle MR images. In this way the MR-visible device can be guided to the target.

A further version of the method in accordance with the invention is characterised in that for guiding the MR visible invasive device along the anticipated trajectory the method comprises a step of introducing an MR visible invasive device in the body while the MR visible invasive device remains simultaneously imaged in both the first and second entry angle MR images. In this way the MR visible invasive device is visible in both the first and second entry angle images and can be guided by taking in account deviations in the two planes.

The invention relates also to an MR-system comprising an MR imaging device and an MR-visible invasive device characterised in that the MR imaging device is arranged for collection of MR images of a first portion of the body, and for obtaining entry MR-images of an MR-visible device and a first portion of the body comprising, at least, a part of an nominal trajectory between the target and the nominal entry point in order to perform the methods of this invention and to obtain the mentioned advantages. These and other, more detailed, aspects of the invention will now be described and illustrated with reference to the Figures.

DETAILED DESCRIPTION OF THE PREFERRED EMBODIMENT

Figure 1:
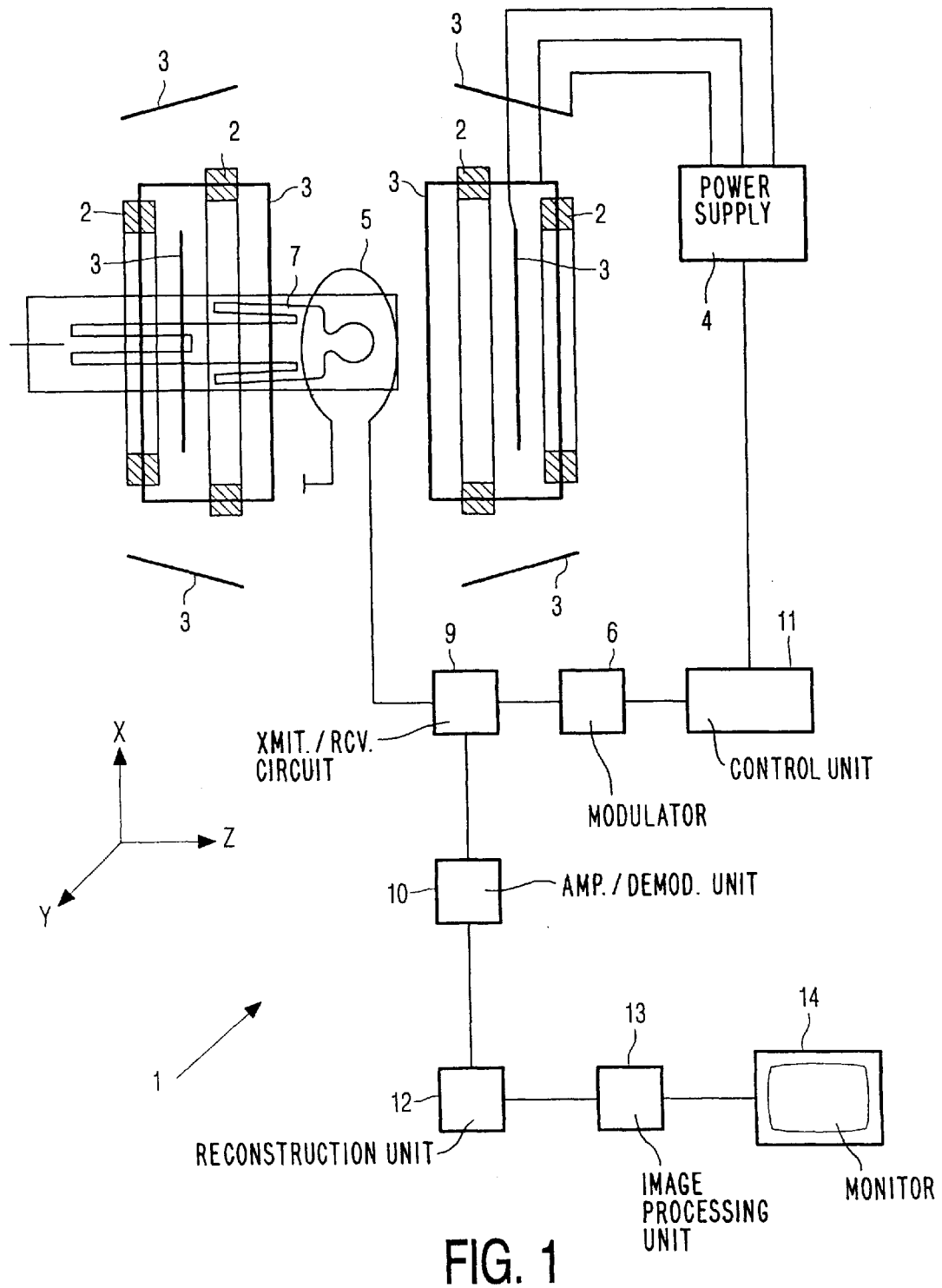
FIG. 1 shows an MR apparatus.

FIG. 1 shows an embodiment of an MR apparatus 1. The MR apparatus 1 comprises a first magnet system 2 for generating a steady magnetic field. The z-direction of the co-ordinate system shown corresponds to the direction of the steady magnetic field in the magnet system 2. The MR apparatus also comprises a second magnet system 3 for generating temporary magnetic fields directed in the z-direction and gradients in the x, y and having z direction, respectively. It is to be noted that for ease of argument x, y and z are used for the frequency encode, phase encode and selection direction, respectively. These directions do not have to coincide with the main directions of the system. Furthermore, in this Application the temporary gradient fields having a gradient in the x-direction, the y-direction and the z-direction are referred to as read gradient, phase-encode gradient and slice-selection gradient, respectively. Power supply means 4 feed the second magnet system 3. The magnet system 2 encloses an examination space which is large enough to accommodate a part of an object 7 to be examined, for example a part of a human body. An RF transmitter coil 5 serves to generate RF magnetic fields and is connected via a transmitter/receiver circuit 9 to an RF source and modulator 6. The RF transmitter coil 5 is arranged around the part of the body 7 in the examination space. The MR apparatus also comprises a receiver coil which is connected via the transmitter/receiver circuit 9 to a signal amplification and demodulation unit 10. The receiver coil and the RF transmitter coil 5 may be one and the same coil. A control unit 11 controls the modulator 6 and the power supply means 4 in order to generate MR imaging sequences comprising RF-pulses and temporary magnetic gradient fields. After excitation of nuclear spins in a part of the body placed within the examination space, the receiver coil 5 receives an MR signal. The phase and amplitude derived therefrom are sampled and further processed in the amplification and demodulation unit 10. An image reconstruction unit 12 processes the MR signals presented so as to form an image. The image is displayed via an image processing unit 13 for example on a monitor 14. The control unit 11 also controls the image reconstruction unit 12. Furthermore, the MR system comprises an MR visible device, for example an MR visible localizer, MR visible pen or an MR visible invasive device.

In a first embodiment of the method according to the invention a collection of pre-intervention MR images is obtained from a first portion of the body, for example, a head of the body to identify a target lesion and sensitive tissue in the head in the vicinity of the lesion. MR imaging sequences employed for collection of MR signals for reconstruction of the pre-intervention MR images are, for example, Fast Field Echo (FFE) imaging sequences. Other possible imaging sequences are, for example, Echo Planar Imaging (EPI) imaging sequences or Turbo Spin Echo (TSE) sequences. Fast Field Echo imaging sequences, EPI imaging sequences and TSE imaging sequences are all known from Magnetic Resonance Imaging, by M. T. Vlaardingerbroek et al, Spinger Verlag, 1995. In a next step an operator selects an anticipated trajectory between a target in the body and an entry point in the part of the body from the collection of pre-intervention images. For establishing of the anticipated trajectory between the target and the entry point in the body at the instant before the intervention according to the invention, the body is positioned in the magnet room and further steps are performed to obtain entry MR-images of an MR-visible localizer and a first portion of the head of the body comprising a part of the nominal trajectory between the target and the surface. Preferably, the first portion comprises a first slab parallel to the surface. For the collection of the MR signals of the entry images, for example, the FFE imaging sequences, can be employed. The FFE imaging sequences are repeated to collect MR signals for the reconstruction of for example 2 to 5 images per second. The establishing of the entry point is elucidated by reference to FIG. 2.

Figure 2:
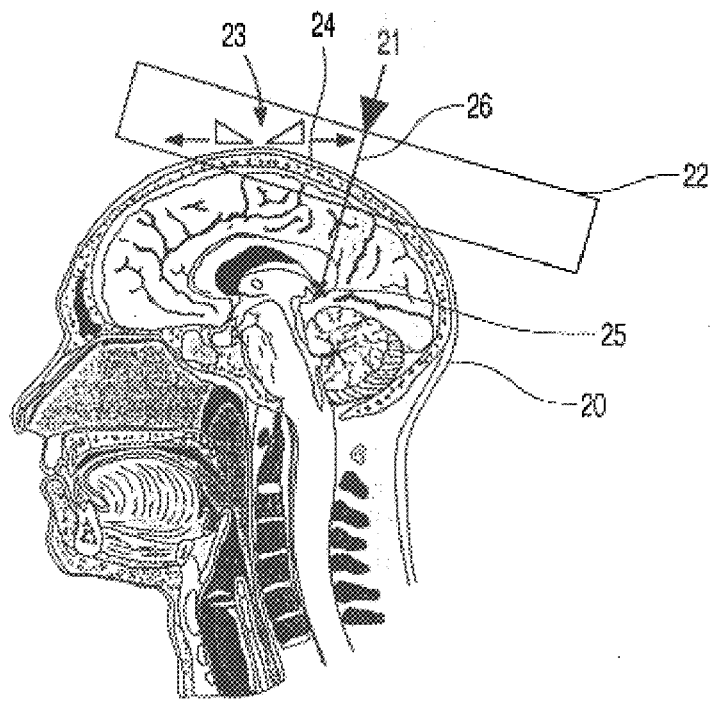
FIG. 2 shows an image of a slab and an entry point of a head of a body.

FIG. 2 shows an example of entry MR image of the head of a body. Furthermore, the entry point 21 and the MR visible localizer 23 are shown. The intersection of the slab and the skull is shown by rectangle 22. To establish an actual entry point the reconstructed entry images are displayed on the monitor 14. Preferably, the entry images are displayed on the monitor 14 such that the entry point is located at the center of the image on the monitor. To identify the entry point in the entry images a marker can be superposed at the position of the entry point 21 represented in the displayed entry-images. Such a marker comprises, for example white or black cross-hair lines.

To determine the entry point the MR-visible localizer 23 is moved over the surface 24 of the body. In this way the entry point 21 and the anticipated trajectory 26 between the entry point 21 and the target 25 just before the instant of the intervention can be determined from the entry-images on the monitor 14 taking in account that the anticipated trajectory hits the target 25 while sensitive structures within the skull are not intersected. Sensitive structures of the skull are, inter alia, major brain vessels or brain tissue with essential functionality. Additionally, a separate pre-intervention anatomical image or angiogram can be visualised as an overlay on the entry images to indicate the position of the major vessels.

The MR-visible localizer 23 comprises for example of a ring either composed of a concentric rings or a circular symmetrical wedge-shape body comprising an MR visible substance. An example of an MR visible localizer is shown in FIG. 3 and FIG. 4.

Figure 3:
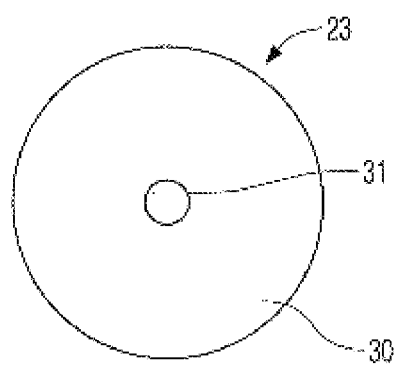
FIG. 3 shows a top view of a MR visible device.
Figure 4:
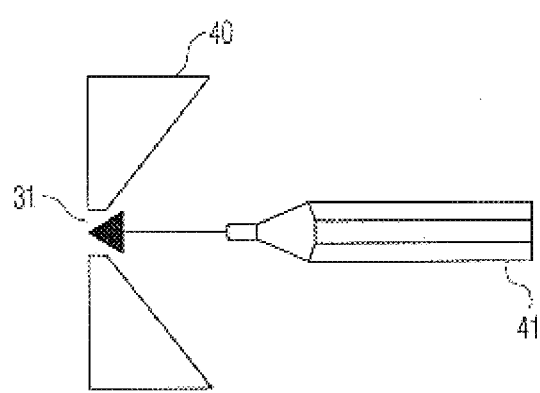
FIG. 4 shows a cross section of the MR visible device.

FIG. 3 shows a top view of a MR visible localizer 23 comprising a single ring 30 having a central orifice 31. FIG. 4 shows an cross section 40 through the MR visible localizer 23. The ring contains for example an MR visible substance comprising a $NiCl_2$-solution in water having a longitudinal relaxation time $T_1$ of 50 ms and a transversal relaxation time $T_2$ of 45 ms. The central orifice can be used for marking the skin with a pen 41 or a needle. Alternatively, the ring 30 could be provided with fixating means to fixate it to the body's skin or skull. Another possibility is that the ring is attached to an external arm fixated to the MR apparatus or external world.

In order to improve the visualisation of the position of the MR-visible localizer 23 the MR imaging sequences to collect the MR-signals for reconstructing the entry-images can be optimised to suppress or enhance different tissue type. For example, Fast Field Echo imaging sequences comprising excitation RF pulses having a flip angle of 20 degrees can be employed. Another example of suitable MR imaging sequences for the entry imaging are slice-selective projection MR angiogram sequences. such as a version of the FFE imaging sequence comprising excitation RF pulses having a flip angle of 90 degrees.

Furthermore, the image processor 13 can be arranged to analyse the image and automatically determine the position of the MR-visible localizer 23. This information can be used to reduce the field of view of the MR imaging sequences for the collection of MR30-signals for the reconstruction of entry image, when the MR visible localizer 23 is closing on the entry point 21 and thereby increase the spatial accuracy.

Figure 9:
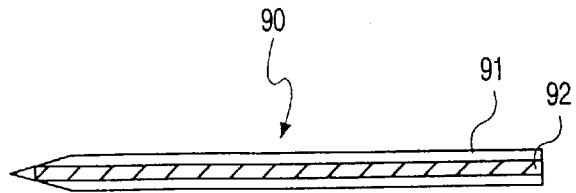
FIG. 9 shows an example of an MR visible pen.

When the entry point is established an entry angle can be established, at which entry angle an MR visible pen can be aligned to the anticipated trajectory. To establish the entry angle in a further version of the method according to the invention first entry angle MR images are obtained from a second slab of the body comprising the anticipated trajectory and a first area near the entry point. These further steps are elucidated with reference to FIG. 5. An example of an MR visible pen for use in the method according to the invention is shown in FIG. 9.

Figure 5:
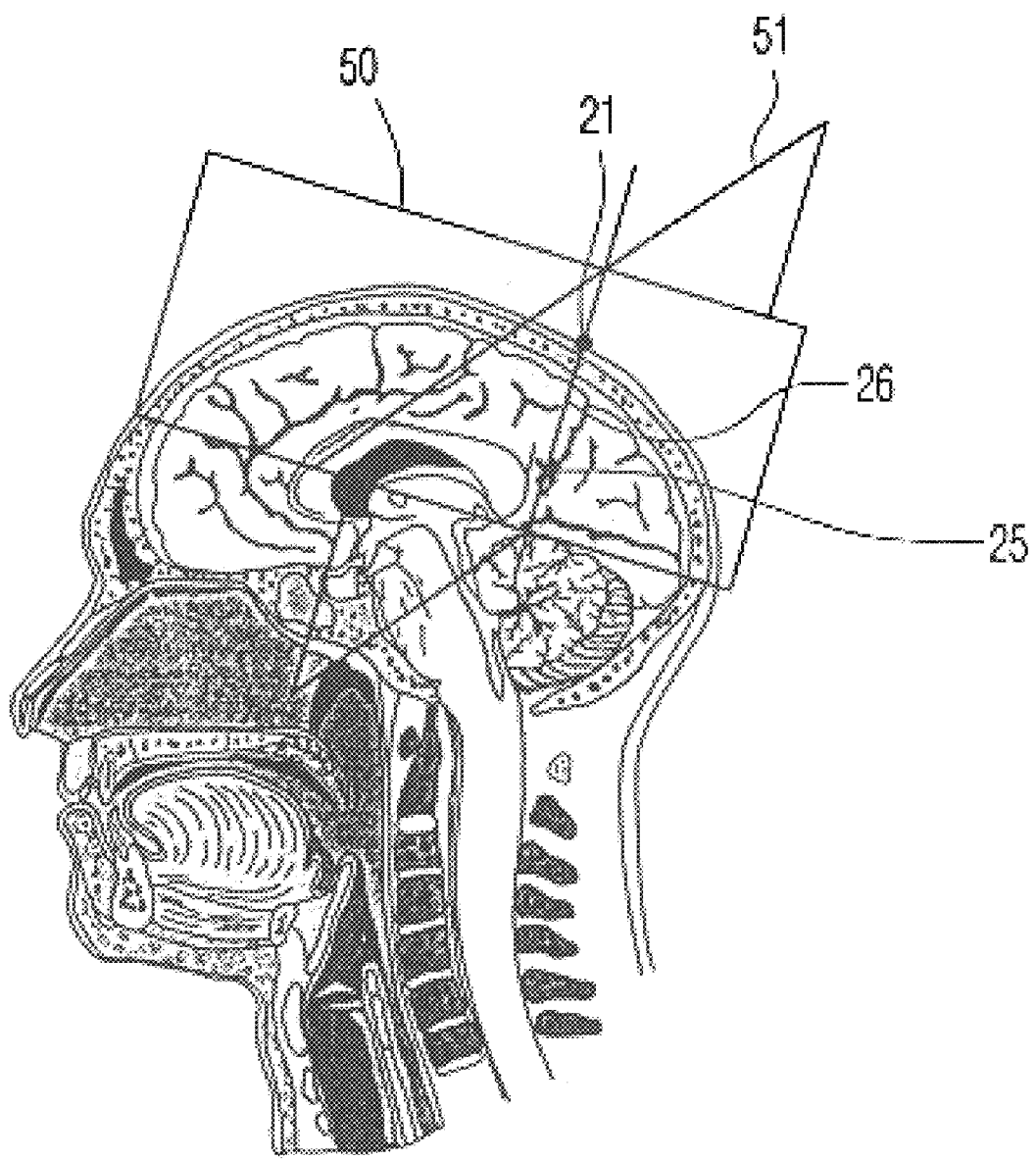
FIG. 5 shows two orthogonal slabs and an intersecting line representing the anticipated trajectory.

FIG. 5 shows an example of a second slab imaged in the first entry images. The second slab indicated by a rectangle 50, comprises the anticipated trajectory 26 between the entry point 21 and the target 25. For example, the FFE sequences can be used also to collect the MR signals for the reconstruction of the first entry angle images. The image reconstruction unit 12 reconstructs the first entry angle images from the collected signals. The image processor 13 displays the first entry angle images on the monitor 14. Then the image processor 13 draws a line 26 between the entry point 21 and the target 25 in the first entry angle MR images representing the anticipated trajectory in the first entry angle MR image, as shown in FIG. 5, and an operator manipulates the MR-visible pen at the actual entry point 21 such that the MR visible pen becomes aligned with the line 26. This manipulation of the MR visible pen 90 (FIGS. 6, 7, 9) can be done by hand or by a targeting device. An example of a targeting device 60 and some details of it are described with respect to FIGS. 6, 7 and 8.

In order to improve the entry angle of the MR visible pen 90 at the actual entry point the version of the method according to the invention can be extended with a step of obtaining a second entry angle image from a third slab of the body comprising the anticipated trajectory and a second area near the entry point, the third slab intersecting the second slab through the anticipated trajectory. FIG. 5 also shows an example of a third slab 51 of the second entry images. The third scan plane 51 is, preferably chosen mutually orthogonal to the second slab 50 and comprises the anticipated trajectory 26 as the intersection between the second and third slabs 50,51. In order to see the anticipated trajectory the image processor 13 displays, for example, both the first and second entry images on the monitor 14 and draws the line 26 representing the anticipated trajectory in the first and second entry angle images. In order to adjust the MR visible pen 90 at the correct entry angle the operator is then manipulating the MR visible pen 90 at the actual entry point 21 such that the MR visible pen is simultaneously imaged in both the first and second entry angle images. In this way the MR visible pen 90 is only imaged in both the first and second entry angle images when it is aligned correctly. Once both the entry point and the entry angle are set the MR visible pen 90 can be replaced by an MR visible invasive device, for example an MR visible needle.

For guiding the MR visible needle to the target along the anticipated trajectory during the actual intervention first entry images are obtained from the second slab comprising the anticipated trajectory. The image processor 13 displays the first entry images on the monitor 14 and draws the line which represents the anticipated trajectory in the first entry images on the monitor and the operator introduces the MR-visible needle in the body while the MR-visible device remains aligned with the line in the first entry images. Alternatively, both first and second entry images can be obtained before and during the intervention from the second and third slab. To display the anticipated trajectory the image processor 13 displays, for example, both the first and second entry images on the monitor 14 and the operator introduces the MR visible needle in the body while the MR visible needle remains simultaneously imaged in both the first and second entry angle images. In this way the operator gets proportional information of the matching of the MR visible needle with the anticipated trajectory. The MR visible needle is completely visible in both the first and second entry angle images when it is perfectly matched with the anticipated trajectory and proportional visibility in the first or second entry angle images corresponding to a deviation with the anticipated trajectory.

In order to accelerate the procedure for adjustment of image parameters of the MR apparatus for obtaining the first entry images, the first and second entry angle images the MR apparatus can be provided with a remote control device. So, the operator can stay near the body to make adjustments of the parameters.

Figure 6:
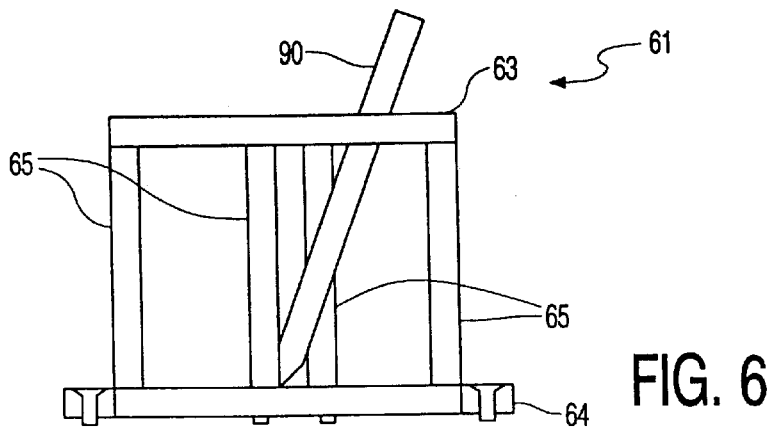
FIG. 6 shows an example of a targeting device.

FIG. 6 shows an example of the targeting device 60 comprising a frame 61 and the MR visible pen 90 for use in the method in accordance with the invention. The frame 61 comprises a moveable guide 62 for positioning the MR visible pen 90, a guide plate 63 for co-operating with the moveable guide 62 and a base plate 64. The guide plate 63 and the base plate 64 being connected to each other by parallel rods 65. The frame is made of a non-metallic material, for example carbon fibre, ceramics or a synthetic material like for example Delrin.

Figure 7:
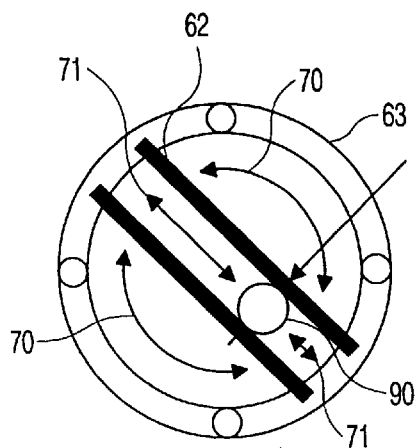
FIG. 7 shows a moveable guide and a guide plate of the targeting device.

FIG. 7 shows the moveable guide 62 and the guide plate 63. Furthermore, first arrows 70 indicate a rotation of the guide and second arrows 71 indicate the translations of the MR visible pen 90. The moveable guide 62 is able to rotate the MR visible pen 90 with respect to a first axis perpendicular to the base plate 64 of the targeting device and a second axis parallel to the base plate 64 and to translate the MR visible pen 90 in a plane parallel to the base plate 64. The targeting device 60 can also be provided with driving means (not shown) for rotating the MR visible pen 90 with respect to the first and second axes and to translate the MR visible pen 90. The driving means may be connected to a remote control receiver for receiving commands from an remote control device controlled by the operator.

Figure 8:
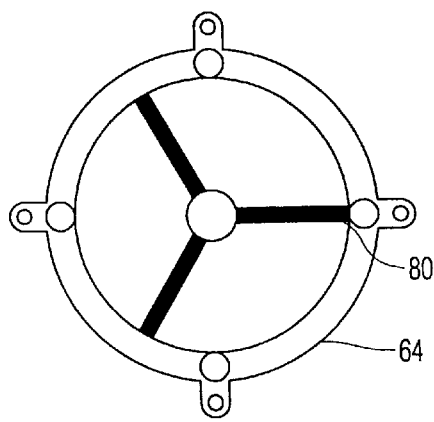
FIG. 8 shows a base plate and a suspension of the targeting device.

FIG. 8 shows the base plate and a suspension 80 for the fixation of a distal end of the MR visible needle at the entry point. The targeting device can be fixated over the determined actual entry point by connecting it to, for example the external arm associated with the MR apparatus, or by attaching the targeting device to the skull directly. Furthermore, the targeting device 60 can be provided with a slide sleeve (not shown in the figures) for guiding the MR visible needle.

FIG. 9 shows the MR visible pen 90 comprising of a housing 91 provided with a channel 92 centred along a length of the pen, the channel 92 contains a MR visible substance. The MR visible substance comprises, for example $NiCl_2$ solution in water having a longitudinal relaxation time $T_1$ of 50 ms and a transversal relaxation time $T_2$ of 45 ms.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An MR system for establishing an anticipated trajectory for an intervention in a body in an examination zone, the anticipated trajectory being in a first portion of the body between an entry point on the body and a target in the body, the MR system comprising:

means for generating a static magnetic field in the examination zone, means for generating RF pulses in the examination zone, means for generating magnetic field gradient pulses in the examination zone, means for receiving MR-signals from the examination zone, processing means for processing received signals into an image, a control unit for generating control signals for the means for generating RF-pulses, the means for generating magnetic field gradient pulses, the means for receiving MR signals, and means for establishing the anticipated trajectory by obtaining one or more pre-intervention MR images including images of the first portion of the body with the target from which the anticipated trajectory for the intervention is selected, wherein the first portion of the body comprises a slab parallel to a surface of the body containing the entry point of the anticipated trajectory, obtaining one or more entry MR-images including images of an MR-visible device positioned substantially at the entry point and of at least a part of the anticipated trajectory near the entry point, and manipulating the MR-visible device so that it is substantially aligned with the anticipated trajectory according to information from the entry MR images on its actual orientation, whereby the anticipated trajectory for the intervention can be established from the alignment of the MR-visible device in real-time MR images just before the instant of intervention.

2. A method for establishing an anticipated trajectory for an intervention in a body, the anticipated trajectory being in a first portion of the body between an entry point on the body and a target in the body, the method comprising:

obtaining one or more pre-intervention MR images including images of the first portion of the body with the target, wherein the first portion of the body comprises a slab parallel to a surface of the body containing the entry point of the anticipated trajectory, selecting the anticipated trajectory for the intervention from the pre-intervention MR images, obtaining one or more entry MR images including images of an MR-visible device positioned substantially at the entry point and of at least a part of the anticipated trajectory near the entry point, and manipulating the MR-visible device so that it is substantially aligned with the anticipated trajectory according to information from the entry MR images on its actual orientation, whereby the anticipated trajectory for the intervention can be established from the alignment of the MR-visible device in real-time MR images just before the instant of intervention.

3. A method according to claim 2 wherein the entry MR images further comprise one or more first entry angle MR images of a different second portion of the body comprising the anticipated trajectory and an area near the entry point, and wherein the step of manipulating further comprises drawing a line in one or more of the first entry angle MR images representing the anticipated trajectory, and aligning the MR visible device with the drawn line.

4. A method according to claim 3 wherein the MR-visible device comprises an MR visible invasive device, and wherein the method further comprises a step of introducing the MR visible invasive device in the body while the MR visible invasive device remains aligned to the drawn line in the first entry angle MR images.

5. The method of claim 2 wherein the entry MR images further comprise one or more images of an MR-visible localizer, and wherein the method further comprises a step of superimposing the MR-visible localizer on the surface of the body at the position of the entry point according to information from the entry MR images, whereby the anticipated trajectory for the intervention can be established from the position of the MR-visible localizer in real-time MR images just before the instant of intervention.

6. The method of claim 5 wherein in the entry images with the superimposed MR-visible localizer the entry point is identified as being within a circularly symmetric MR-visible indicia.

7. A method for establishing an anticipated trajectory for an intervention in a body, the anticipated trajectory being in a first portion of the body between an entry point on the body and a target in the body, the method comprising:

obtaining one or more pre-intervention MR images including images of the first portion of the body with the target, selecting the anticipated trajectory for the intervention from the pre-intervention MR images, obtaining a plurality of entry MR images including images of an MR-visible device positioned substantially at the entry point and of at least a part of the anticipated trajectory near the entry point, wherein the entry MR images further comprise (i) one or more first entry angle MR images of a second portion of the body comprising the anticipated trajectory and an area near the entry point, and (ii) one or more second entry angle images of a third portion of the body comprising the anticipated trajectory and a second area near the entry point, the third portion of the body intersecting the second portion of the body along the anticipated trajectory, and manipulating the MR-visible device by drawing a line in one or more of the first entry angle MR images representing the anticipated trajectory, and substantially aligning the MR visible device with the drawn line such that the MR visible device is imaged simultaneously in both the first and second entry angle images, whereby the anticipated trajectory for the intervention can be established from the alignment of the MR-visible device in real-time MR images just before the instant of intervention.

8. A method according to claim 7 wherein said second and third portions of the body comprise slabs of the body.

9. A method according to claim 7 wherein the MR-visible device comprises an MR visible invasive device, and wherein the method comprises a further step of introducing the MR-visible invasive device in the body while the MR-visible device remains simultaneously imaged in both the first and second entry angle images.

10. The method of claim 7 further comprising, first, replacing the MR-visible device with an MR-visible invasive device, and, second, introducing the MR visible invasive device in the body.

* * * * *